(12) United States Patent
Kato et al.

(10) Patent No.: US 9,233,082 B2
(45) Date of Patent: Jan. 12, 2016

(54) METHOD FOR SEARCHING FOR MALODOR CONTROL AGENT, MALODOR CONTROL AGENT, AND MALODOR CONTROL METHOD

(75) Inventors: Aya Kato, Haga-gun (JP); Naoko Saito, Haga-gun (JP); Etsuji Wakisaka, Chuo-ku (JP)

(73) Assignee: Kao Corporation, Tokyo (JP)

( * ) Notice: Subject to any disclaimer, the term of this patent is extended or adjusted under 35 U.S.C. 154(b) by 71 days.

(21) Appl. No.: 13/819,882

(22) PCT Filed: Sep. 1, 2011

(86) PCT No.: PCT/JP2011/069939
§ 371 (c)(1),
(2), (4) Date: Feb. 28, 2013

(87) PCT Pub. No.: WO2012/029922
PCT Pub. Date: Mar. 8, 2012

(65) Prior Publication Data
US 2013/0216492 A1    Aug. 22, 2013

(30) Foreign Application Priority Data

Sep. 3, 2010   (JP) .................................. 2010-197759
Sep. 3, 2010   (JP) .................................. 2010-197825

(51) Int. Cl.
| | | |
|---|---|---|
| *A61K 31/11* | (2006.01) | |
| *C12Q 1/66* | (2006.01) | |
| *G01N 33/50* | (2006.01) | |
| *G01N 33/566* | (2006.01) | |
| *G01N 33/74* | (2006.01) | |

(52) U.S. Cl.
CPC . *A61K 31/11* (2013.01); *C12Q 1/66* (2013.01); *G01N 33/5058* (2013.01); *G01N 33/566* (2013.01); *G01N 33/74* (2013.01); *G01N 2333/726* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 7,344,845 B2 * | 3/2008 | Han et al. ..................... | 435/7.21 |
| 2003/0207337 A1 | 11/2003 | Han et al. | |
| 2003/0211960 A1 | 11/2003 | Smets | |
| 2003/0228992 A1 | 12/2003 | Smets et al. | |
| 2004/0097397 A1 | 5/2004 | Mohr et al. | |
| 2006/0014655 A1 | 1/2006 | Smets et al. | |
| 2008/0032910 A1 | 2/2008 | Smets et al. | |
| 2008/0299586 A1 * | 12/2008 | Han et al. ..................... | 435/7.21 |
| 2011/0071070 A1 | 3/2011 | Kotachi et al. | |
| 2014/0186864 A1 | 7/2014 | Kato et al. | |

FOREIGN PATENT DOCUMENTS

| | | | |
|---|---|---|---|
| JP | 04-178319 | A | 6/1992 |
| JP | 2003-113392 | A | 4/2003 |
| JP | 2003-518162 | A | 6/2003 |
| JP | 2003-190264 | A | 7/2003 |
| JP | 2004-504010 | A | 2/2004 |
| JP | 2004-203782 | A | 7/2004 |
| JP | 2004-262900 | A | 9/2004 |
| JP | 2004-263102 | A | 9/2004 |
| JP | 2007-070269 | A | 3/2007 |
| JP | 2007-230982 | A | 9/2007 |
| JP | 2008-274040 | A | 11/2008 |
| JP | 2009-209326 | A | 9/2009 |
| JP | 2010-215529 | A | 9/2010 |
| WO | WO 01/46365 | A2 | 6/2001 |
| WO | WO 01/68805 | A2 | 9/2001 |
| WO | WO 01/98526 | A2 | 12/2001 |
| WO | WO 01/68805 | A2 | 1/2003 |

OTHER PUBLICATIONS

Malnic, et al, Supporting Information Table 5 downloaded Jan. 23, 2015 from the website: http://www.pnas.org/content/suppl/2004/02/03/0307882100.DC1/7882Table5.html.*
NCBI Summary, Human olfactory receptor OR5I2 downloaded Jan. 23, 2015 from the website: http://www.ncbi.nlm.nih.gov/gene/390064.*
NCBI Summary, Human olfactory receptor OR5I1 downloaded Jan. 23, 2015 from the website: http://www.ncbi.nlm.nih.gov/gene/119682.*

(Continued)

*Primary Examiner* — Frederick Krass
*Assistant Examiner* — Michael P Cohen
(74) *Attorney, Agent, or Firm* — Sterne, Kessler, Goldstein & Fox P.L.L.C.

(57) ABSTRACT

Provided are a method for searching for a malodor inhibitor by using the response of an olfactory receptor as an indicator; a method for inhibiting malodor based on the antagonism of olfactory receptors; and a malodor inhibitor. Disclosed are a method for searching for a malodor inhibitor, the method including: adding a test substance and a malodor-causing substance to any one olfactory receptor selected from the group consisting of OR51E1, OR2W1, OR10A6, OR5I2, and OR51L1, measuring the response of the olfactory receptor to the malodor-causing substance, identifying the test substance that suppresses the response of the olfactory receptor on the basis of the measured response, and selecting the identified test substance as a malodor inhibitor; an antagonist to any one olfactory receptor selected from the group consisting of OR51E1, OR2W1, OR10A6, OR5I2, and OR51L1; a method for inhibiting malodor using the antagonist.

11 Claims, 8 Drawing Sheets

(56) References Cited

OTHER PUBLICATIONS

Harumi Saito, Qiuyi Chi, Hanyi Zhuang, Hiro Matsunami, and Joel D. Mainland. Odor Coding by a Mammalian Receptor Repertoire. Sci Signal. 2009, 2(60), pp. 1-28. (Authors Manuscript).*
International Search Report (ISR) for PCT/JP2011/069939; I.A. fd: Sep. 1, 2011, mailed Dec. 6, 2011 from the Japanese Patent Office, Tokyo, Japan.
International Preliminary Report on Patentability (IPRP), Chapter I of the Patent Cooperation Treaty, including the Written Opinion for PCT/JP2011/069939; I.A. fd: Sep. 1, 2011, issued Apr. 9, 2013, from the International Bureau of WIPO, Geneva, Switzerland.
Kawasaki, M. et al., in "Sense of smell and a smell material," pp. 127-129, published by Sep. 20, 1998, Takashi Okawa, publisher, Soran Company.
Saito, H et al., "Odor coding by a mammalian receptor repertoire," Sci Signal, Mar. 2009, vol. 2, No. 60, ra9, pp. 1-14, Amrican Assoc for the Adv of Sci, Washington, DC.
Philippeau, M et al., "Identification and characterization of a carboxylic acid-responding human OR," AChemS Abstracts 2009, pp. 64-65, Abstract No. P121, 31$^{st}$ Annual Meeting of the Assoc for Chemoreception Sciences, Apr. 22-26, 2009, Sarasota, Florida.
Oka, Y et al., "Kyukaku Juyotai Antagonist no Dotei to Seiriteki Igi", The identification of the sense of the smell receptor antagonist and physiologic significance, Japan Society for Bioscience, Biotechnology, and Agrochemistry Taikai Koen Yoshishu, 2003, vol. 2003$^{rd}$, p. 152, No. 3A04p18.
Oka, Y et al., "Olfactory receptor antagonism between odorants," EMBO J, Jan. 2004; 23(1): 120-126, Nature Pub. Group, London, England.
Malnic, B et al., Definition: Olfactory receptor 5I2 [*Homo sapiens*]., Database DDBJ/EMBL/GenBank [online], Accession No. NP_001004754, Mar. 5, 2010 uploaded, retrieval date Nov. 16, 2011 <http://www.ncbi.nlm.nih.gov/protetin/52317265?sat=14&satkey=4237020>.
Malnic, B et al., Definition: Olfactory receptor 10A6 [*Homo sapiens*]., Database DDBJ/EMBL/GenBank [online], Accession No. NP_001004461, May 7, 2010 uploaded, retrieval date Nov. 16, 2011 <http://www.ncbi.nlm.nih.gov/protetin/52218836?sat=14&satkey=2374644>.
Sanz, G et al., "Comparison of Odorant Specificity of Two Human Olfactory Receptors from Different Phylogenetic Classes and Evidence for Antagonism," Chem Senses, Jan. 2005; 30: 69-80, Oxford University Press, London, England.
Extended European search report for EP Patent Appl. No. 11821937.7, mailed Feb. 3, 2014 from the European Patent Office, Rijswijk, Netherlands.
Malnic, B et al., "The human olfactory receptor gene family," Proc. Natl. Acad. Sci. USA, Feb. 2004; 101: 2584-2589, National Academy of Sciences, Washington, DC.
'Partial European search report for EP Patent Appl. No. 14180992.1, mailed Feb. 19, 2015 from the European Patent Office, Munich, Germany.
Malnic, B et al., "The human olfactory receptor gene family," Proc. Natl. Acad. Sci. 'USA, Feb. 2004; 101: 2584—2689, National Academy of Sciences, Washington, DC.

* cited by examiner

METHOD FOR SEARCHING FOR MALODOR CONTROL AGENT, MALODOR CONTROL AGENT, AND MALODOR CONTROL METHOD

REFERENCE TO SEQUENCE LISTING SUBMITTED ELECTRONICALLY

The content of the electronically submitted substitute sequence listing, file name 25370820002sequencelisting.txt, size 24,212 bytes; and date of creation Apr. 17, 2013, filed herewith, is incorporated herein by reference in its entirety.

FIELD OF THE INVENTION

The present invention relates to a method for searching for a malodor inhibitor, a malodor inhibitor, and a method for inhibiting malodor.

BACKGROUND OF THE INVENTION

In our living environment, there are a large number of malodorous molecules having different polarization characteristics and molecular weights. Hitherto, a variety of methods have been developed for reducing various malodorous molecules. Generally, the methods for reducing malodors are broadly classified into a biological method, a chemical method, a physical method, or a sensory method. Among malodorous molecules, short-chain fatty acids and amines, having high polarity, can be reduced through a chemical method; i.e., neutralization. Sulfur-containing compounds such as thiol can be reduced through a physical method; i.e., adsorption. However, there still remain many malodorous molecules, such as medium-chain and long-chain fatty acids and skatole, which cannot be reduced through known malodor reducing techniques.

In mammals including humans, the mechanism for odorant recognition includes binding odorant molecules to olfactory receptors present on olfactory sensory neurons included in the olfactory epithelium, which is present in an upper portion of the nasal cavity, and transmitting the response of the receptors to the central nervous system. It has been reported that, 387 different olfactory receptors are present in human, and the genes encoding these olfactory receptors account for about 3% of the human genome.

Generally, a plurality of olfactory receptors responds to a plurality of odorant molecules. Specifically, one single olfactory receptor responds to a plurality of structurally similar odorant molecules at different affinities, while one single odorant molecule is detected by a plurality of olfactory receptors. It is also reported that a certain odorant molecule which can activate one olfactory receptor serves as an antagonist that inhibits activation of another olfactory receptor. Such combined response of these olfactory receptors leads to recognition of each odor.

Therefore, even in the case where the same odor molecules are present, if other odor molecules exist simultaneously, the receptor response may be inhibited by the other odor molecules, and the odor that is eventually perceived may come out to be completely different. Such a mechanism is referred to as the antagonism of olfactory receptors. Modification of an odor by this antagonism of receptors can specifically cause loss of the perception of a malodor, unlike the deodorization methods involving addition of another odor such as the odor of a perfume or an aromatizing agent. Furthermore, there is no chance of occurrence of any unpleasant feelings caused by the odor of the aromatizing agent.

In regard to nonanoic acid, hexanoic acid, isovaleric acid and the like, which are representative causative substances for body odor, their odors have been hitherto disodorized or deodorized by techniques such as the use of a disodorizer or a deodorizer, and the use of a fragrance or an aromatizing agent (Patent Documents 1 and 2, and Non-Patent Document 1). However, these techniques are methods intended to reduce the initial generation of an odorous substance or to make another odor to be more strongly perceived, and these methods differ from the deodorization by masking based on the antagonism of olfactory sensors. Furthermore, in the conventional methods, when a deodorizer is used, since some time is required to reduce the odorous substance, the methods lack immediate effectiveness. When an aromatizing agent is used, there are occasions in which unpleasant feelings may occur due to the odor of the aromatizing agent itself. In other cases, the conventional methods may even eliminate odors other than an intended malodor. If deodorization by masking based on the antagonism of olfactory receptors is utilized, there is a possibility that the problems described above may be solved.

In order to utilize the antagonism of olfactory receptors, there is a need for a search and identification of substances which exhibit olfactory receptor antagonistic action against individual malodor molecules; however, it is not easy to conduct such a search. Conventionally, the evaluation of an odor has been carried out by a sensory test conducted by experts. However, a sensory test has problems such as a need to foster experts who are capable of evaluating odors, and the characteristic of low throughput.

In order to achieve odor control by utilizing the antagonism of olfactory receptors, it would be an important matter to correlate an odor and an olfactory receptor. In relation to the olfactory receptors that receive nonanoic acid or hexanoic acid, it has been hitherto reported that OR2W1 responds to hexanoic acid and nonanoic acid, OR51E1 responds to nonanoic acid, and OR51L1 responds to hexanoic acid (Non-Patent Document 2). It has also been reported that OR51E1 responds to isovaleric acid (Non-Patent Document 3).

Aldehyde-based fragrance components have been traditionally incorporated into aromatizing/deodorizing agents cleaning compositions and the like for personal care or environment, (Patent Documents 1 to 3). However, these components are used as aromatizing components, and have not been used as antagonists that control the response of olfactory receptors to malodors.

CITATION LISTS

Patent Document

Patent Document 1: JP-A-2003-190264
Patent Document 2: JP-A-2003-113392
Patent Document 3: JP-A-2003-518162

Non-Patent Document

Non-Patent Document 1: KAWASAKI Michiaki and HORIUCHI Tetsushirou, Kyukaku to Nioi Busshitsu (Japan Association on Odor Environment)
Non-Patent Document 2: Saito H., Chi Q., Zhuang H., Matsunami H., Mainland J. D. Sci Signal. (2009, 2 (60): ra9
Non-Patent Document 3: Philippeau et al., ACHEMS 2009 Annual Meeting Abstract, 31$^{st}$ Annual Meeting of the Association for Chemoreception Sciences, #P121

SUMMARY OF THE INVENTION

That is, according to an aspect of the present invention, the present invention a method for searching for a malodor inhibitor, the method including:

adding a test substance and a malodor-causing substance to any one olfactory receptor selected from the group consisting of OR51E1, OR2W1, OR10A6, OR51I2, and OR51L1;

measuring the response of the olfactory receptor to the malodor-causing substance;

identifying the test substance which suppresses the response of the olfactory receptor on the basis of the measured response; and selecting the identified test substance as the malodor inhibitor.

According to another aspect of the present invention, there is provided a compound for use in the antagonism of any one olfactory receptor selected from the group consisting of OR51E1, OR2W1, OR10A6, OR51I2, and OR51L1, the compound being one or more selected from the group consisting of the following compounds: 3-(3-isopropylphenyl)-butyraldehyde, 4-isopropyl-1-methylcyclohexanecarbaldehyde, 3-(4-tert-butylphenyl)propanal, 3-(4-isopropylphenyl)-2-methylpropanal, 3,7-dimethyl-7-hydroxyoctanal, p-tert-butyl-α-methylhydrocinnamaldehyde, 7-methoxy-3,7-dimethyloctanal, 3-(4-isobutylphenyl)-2-methyl-propionaldehyde, 4-isopropyl-1-methylcyclohexylmethanol, 4-(2-methoxyphenyl)-2-methyl-2-butanol, tetrahydro-4-methyl-2-(2-methylpropyl)-2H-pyran-4-ol, 2,2-dimethyl-3-(3-methylphenyl)propanol, 4-isopropylcyclohexanecarbaldehyde, 3,7-dimethyl-6-octenal, 1,2,3,4,5,6,7,8-octahydro-8,8-dimethyl-2-naphthalenecarboxy aldehyde, 2,4,6-trimethyl-3-cyclohexene-1-carboxyaldehyde, 3,5,6-trimethyl-3-cyclohexene-1-carboxyaldehyde, 2,4-dimethyl-3-cyclohexane-1-carboxyaldehyde, 4-isopropylbenzaldehyde, and 2-cyclohexylpropanal.

According to another aspect of the present invention, there is provided an olfactory receptor antagonist for use in the malodor inhibition, the antagonist antagonizing any one olfactory receptor selected from the group consisting of OR51E1, OR2W1, OR10A6, OR51I2 and OR51L1 and being one or more selected from the group consisting of the following compounds: 3-(3-isopropylphenyl)-butyraldehyde, 4-isopropyl-1-methylcyclohexanecarbaldehyde, 3-(4-tert-butylphenyl)propanal, 3-(4-isopropylphenyl)-2-methylpropanal, 3,7-dimethyl-7-hydroxyoctanal, p-tert-butyl-α-methylhydrocinnamaldehyde, 7-methoxy-3,7-dimethyloctanal, 3-(4-isobutylphenyl)-2-methyl-propionaldehyde, 4-isopropyl-1-methylcyclohexylmethanol, 4-(2-methoxyphenyl)-2-methyl-2-butanol, tetrahydro-4-methyl-2-(2-methylpropyl)-2H-pyran-4-ol, 2,2-dimethyl-3-(3-methylphenyl)propanol, 4-isopropylcyclohexanecarbaldehyde, 3,7-dimethyl-6-octenal, 1,2,3,4,5,6,7,8-octahydro-8,8-dimethyl-2-naphthalenecarboxy aldehyde, 2,4,6-trimethyl-3-cyclohexene-1-carboxyaldehyde, 3,5,6-trimethyl-3-cyclohexene-1-carboxyaldehyde, 2,4-dimethyl-3-cyclohexane-1-carboxyaldehyde, 4-isopropylbenzaldehyde, and 2-cyclohexylpropanal.

According to still another aspect of the present invention, there is provided a method for inhibiting malodor including causing a malodor and an antagonist to an olfactory receptor for the malodor to coexist, the antagonist being an antagonist to any one olfactory receptor selected from the group consisting of OR51E1, OR2W1, OR10A6, OR51I2, and OR51L1, and being one or more selected from the group consisting of 3-(3-isopropylphenyl)-butyraldehyde, 4-isopropyl-1-methylcyclohexanecarbaldehyde, 3-(4-tert-butylphenyl)propanal, 3-(4-isopropylphenyl)-2-methylpropanal, 3,7-dimethyl-7-hydroxyoctanal, p-tert-butyl-α-methylhydrocinnamaldehyde, 7-methoxy-3,7-dimethyloctanal, 3-(4-isobutyl-phenyl)-2-methyl-propionaldehyde, 4-isopropyl-1-methylcyclohexylmethanol, 4-(2-methoxyphenyl)-2-methyl-2-butanol, tetrahydro-4-methyl-2-(2-methylpropyl)-2H-pyran-4-ol, 2,2-dimethyl-3-(3-methylphenyl)propanol, 4-isopropylcyclohexanecarbaldehyde, 3,7-dimethyl-6-octenal, 1,2,3,4,5,6,7,8-octahydro-8,8-dimethyl-2-naphthalenecarboxy aldehyde, 2,4,6-trimethyl-3-cyclohexene-1-carboxyaldehyde, 3,5,6-trimethyl-3-cyclohexene-1-carboxyaldehyde, 2,4-dimethyl-3-cyclohexane-1-carboxyaldehyde, 4-isopropylbenzaldehyde, and 2-cyclohexylpropanal.

DETAILED DESCRIPTION OF THE INVENTION

Figure 1:
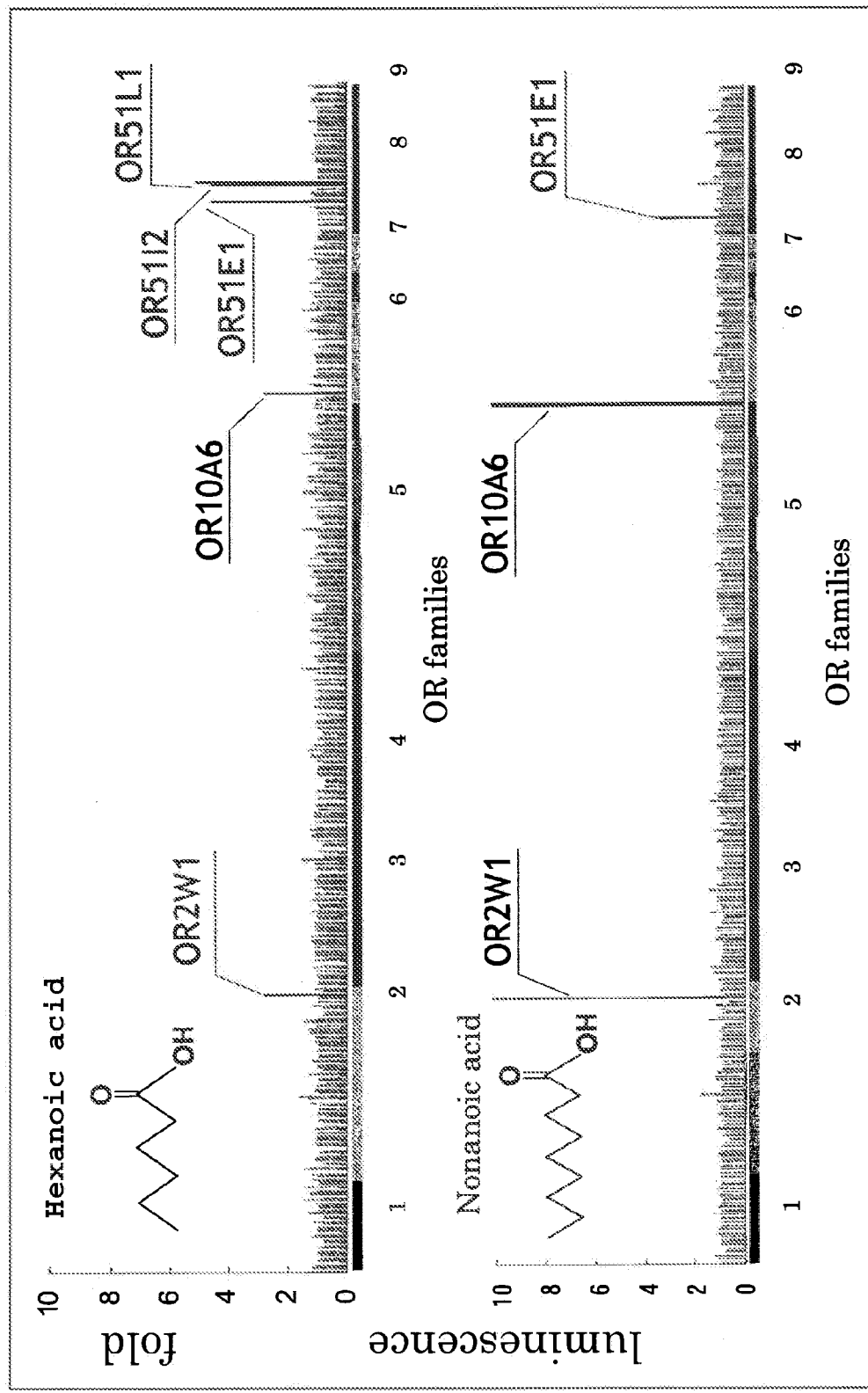
FIG. 1 is a set of diagrams illustrating the responses of olfactory receptors to hexanoic acid and nonanoic acid, in which the horizontal axis illustrates individual olfactory receptors, while the vertical axis illustrates the response intensities.

As used herein, the term "masking" in the odor-related field generally refers to means for inhibiting or weakening recognition of a target odor. The term "masking" may encompass chemical means, physical means, biological means, and sensory means. Examples of the masking means include any means for removing a odorant molecule responsible for a target odor from the environment (e.g., adsorption and chemical decomposition of the odorant); means for preventing release of a target odor to the environment (e.g., sealing); and a method in which recognition of a target odor is inhibited by adding another odorant such as a perfume or an aromatic.

As used herein, the term "masking through olfactory receptor antagonism" refers to one embodiment of the aforementioned broadly defined "masking" and is means for inhibiting the response of an olfactory receptor to a target odorant molecule by an additional odorant molecule, to thereby modulate the smell of the target odorant molecule recognized by a subject. Although masking through olfactory receptor antagonism employs an additional odorant molecule, the masking differs from means for canceling out a target odor by use of a strong odorant such as a perfume. In one embodiment of masking through olfactory receptor antagonism, a substance which can inhibit the response of an olfactory receptor such as an antagonist is used. When a response-inhibiting substance which can specifically inhibit the response of a receptor related to recognition of a certain odor is employed, the response of the receptor is suppressed, whereby the odor recognized by a subject can be modulated.

The present invention provides a method for searching for a malodor inhibitor by using the response of an olfactory receptor as an indicator, a method for inhibiting malodor based on the antagonism of olfactory receptors, and a malodor inhibitor.

The inventors of the present invention succeeded in newly identifying olfactory receptors that respond to malodor-causing substances such as nonanoic acid, hexanoic acid, and isovaleric acid odors. Furthermore, the inventors of the present invention found that substances which control the response of the relevant olfactory receptors can be used as malodor inhibitors that inhibit malodor through masking by means of the antagonism of olfactory receptors. Furthermore, the inventors of the present invention succeeded in identifying olfactory receptors that respond to malodor-causing substances such as nonanoic acid, hexanoic acid, and isovaleric acid, and antagonists to the olfactory receptors. The relevant receptor antagonists can inhibit malodors through masking by means of the antagonism of olfactory receptors. Based on these findings, the inventors completed the present invention.

According to the present invention, there is no problem with low immediate effectiveness or with the unpleasantness originating from the odor of an aromatizing agent, which have occurred in the conventional deodorization method of using a deodorizer or an aromatic agent, and a malodor can be specifically deodorized. Furthermore, according to the present invention, an efficient search for such a malodor inhibitor can be made.

According to an embodiment, the present invention provides a method for searching for a malodor inhibitor. This method includes adding a test substance and a malodor-causing substance to any one olfactory receptor selected from the group consisting of OR51E1, OR2W1, OR10A6, OR51I2, and OR51L1; measuring the response of the olfactory receptor; identifying the test substance which suppresses the response of the olfactory receptor on the basis of the measured response; and selecting the identified test substance as a malodor inhibitor.

In the method of the present invention, a test substance and a substance which causes a malodor are added to an olfactory receptor which responds to the malodor. The olfactory receptor used in the method of the present invention may be any one olfactory receptor selected from the group consisting of OR51E1, OR2W1, OR10A6, OR51I2, and OR51L1.

OR51E1, OR2W1, OR10A6, OR51I2, and OR51L1 are olfactory receptors that are expressed in human olfactory cells, and are respectively registered in GenBank under Accession Nos. GI:205277377, GI:169234788, GI:52218835, GI:284172435, and GI:52317143.

OR10A6 is a protein consisting of the amino acid sequence set forth in SEQ ID NO: 2, which is encoded by a gene having the nucleotide sequence set forth in SEQ ID NO: 1.

OR2W1 is a protein consisting of the amino acid sequence set forth in SEQ ID NO: 4, which is encoded by a gene having the nucleotide sequence set forth in SEQ ID NO: 3.

OR51E1 is a protein consisting of the amino acid sequence set forth in SEQ ID NO: 6, which is encoded by a gene having the nucleotide sequence set forth in SEQ ID NO: 5.

OR51I2 is a protein consisting of the amino acid sequence set forth in SEQ ID NO: 8, which is encoded by a gene having the nucleotide sequence set forth in SEQ ID NO: 7.

OR51L1 is a protein consisting of the amino acid sequence set forth in SEQ ID NO: 10, which is encoded by a gene having the nucleotide sequence set forth in SEQ ID NO: 9.

Furthermore, examples of the olfactory receptors used in the method of the present invention include polypeptides having responsiveness to malodors of nonanoic acid, hexanoic acid, isovaleric acid or the like, each of which comprises an amino acid sequence having a sequence identity of 80% or more, preferably 85% or more, more preferably 90% or more, even more preferably 95% or more, and still more preferably 98% or more, with the amino acid sequence of OR51E1, OR2W1, OR10A6, OR51I2, or OR51L1 described above. In the method of the present invention, any of the olfactory receptors may be used alone, or plural olfactory receptors may be used in combination.

Figure 2:
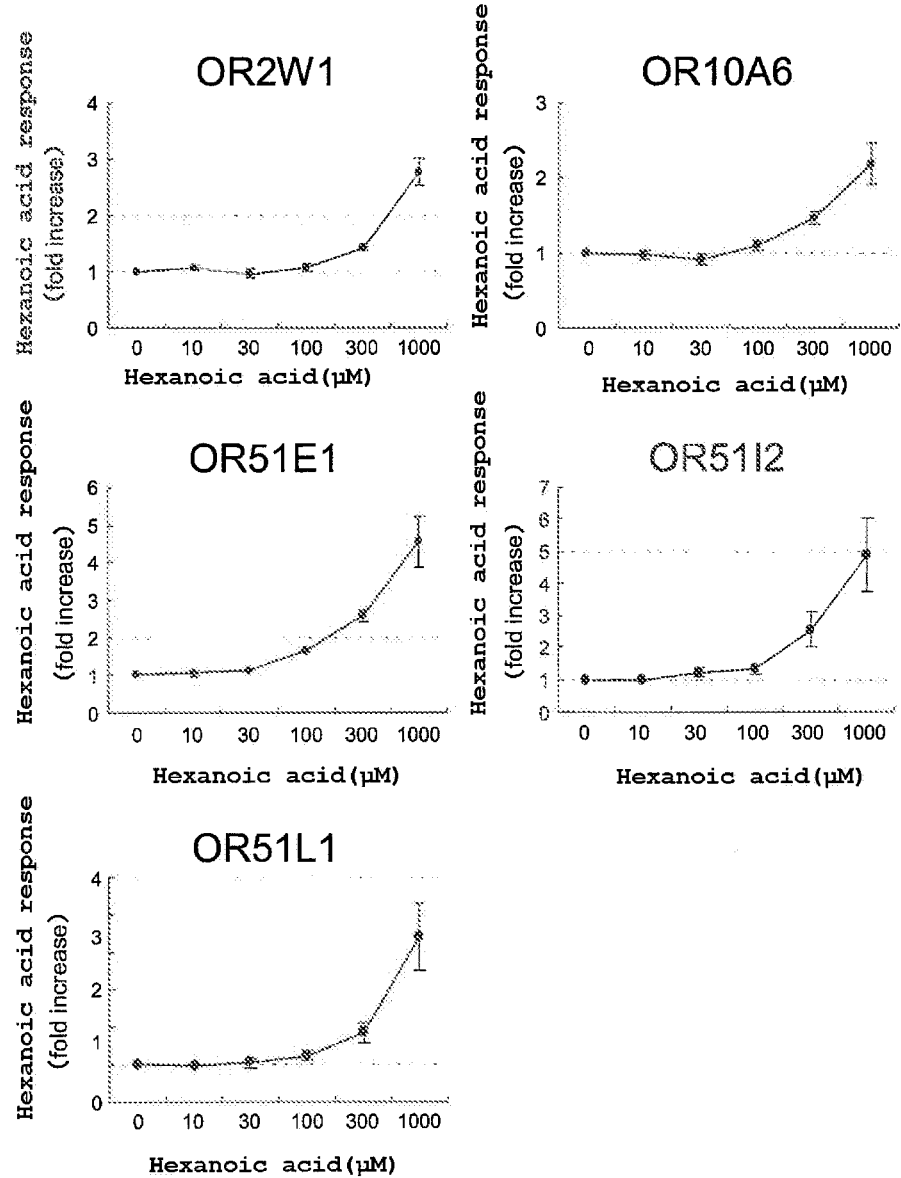
FIG. 2 is a set of diagrams illustrating the responses of olfactory receptors to hexanoic acid of various concentrations, in which an error bar=±SE.
Figure 3:
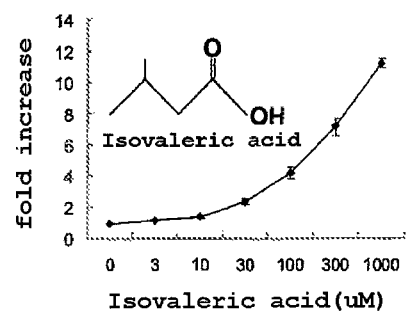
FIG. 3 is a set of diagrams illustrating the responses of olfactory receptors to isovaleric acid of various concentrations, in which an error bar=±SE.
Figure 3:
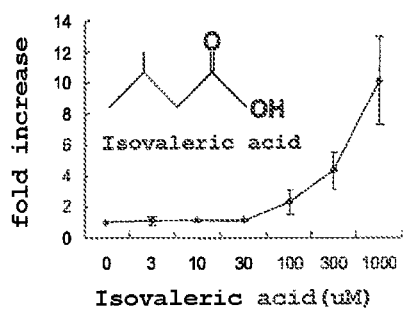

Since the olfactory receptors described above are responsive to nonanoic acid, hexanoic acid, or isovaleric acid as illustrated in FIGS. 1, 2, and 3, a substance which suppresses the response of such a receptor causes a change in the perception of nonanoic acid odor, hexanoic acid odor, or isovaleric acid odor at the central nervous system, through masking based on the antagonism of olfactory receptors, and consequently can inhibit a malodor caused by nonanoic acid, hexanoic acid, or isovaleric acid. Therefore, the malodor-causing substance that is used in the present invention is preferably nonanoic acid, hexanoic acid or isovaleric acid, and examples of the malodor that is inhibited by the malodor inhibitor searched by the method of the present invention include the hexanoic acid odor, the nonanoic acid odor, and the isovaleric acid odor. The hexanoic acid odor, the nonanoic acid odor, and the isovaleric acid odor are generally known as, for example, the odors of the body odor (or fatty acid odors) caused by sweat or sebum, or the like.

Therefore, in the case of searching for an inhibitor for the hexanoic acid odor in the method of the present invention, the olfactory receptor to be used is selected from the group consisting of OR51E1, OR2W1, OR10A6, OR51I2, and OR51L1, and is preferably selected from the group consisting of OR51E1, OR10A6, and OR51I2. The malodor-causing substance to be used is hexanoic acid. Furthermore, in the case of searching for an inhibitor for the nonanoic acid odor in the method of the present invention, the olfactory receptor to be used is selected from the group consisting of OR51E1, OR2W1, and OR10A6, and is preferably OR10A6. The malodor-causing substance to be used is nonanoic acid. Further, in the case of searching for a control agent for the isovaleric acid odor in the method of the present invention, the olfactory receptor to be used is selected from the group consisting of OR51I2 and OR51E1, and is preferably OR51I2. The malodor-causing substance to be used is isovaleric acid.

Alternatively, by using an olfactory receptor which responds to both the hexanoic acid odor and the nonanoic acid odor, a malodor inhibitor which inhibits both the odors can be searched for. In this case, the olfactory receptor to be used is selected from the group consisting of OR2W1, OR10A6, and OR51E1, and the olfactory receptor to be used is preferably OR10A6. Alternatively, by using an olfactory receptor which responds to both the hexanoic acid odor and the isovaleric acid odor, a malodor inhibitor which inhibits both the odors can be searched for. In this case, the olfactory receptor to be used is selected from the group consisting of OR51I2 and OR51E, and the olfactory receptor to be used is preferably OR51I2. Alternatively, by using an olfactory receptor which responds to both the nonanoic acid odor and the isovaleric acid odor, a malodor inhibitor which inhibits both the odors can be searched for. In this case, the olfactory receptor to be used is preferably OR51E1. Alternatively, by using an olfactory receptor which responds to any of the hexanoic acid odor, the nonanoic acid odor, and the isovaleric acid odor, a malodor inhibitor which inhibits the three kinds of odors can be searched for. In this case, the olfactory receptor to be used is preferably OR51E1.

No particular limitation is imposed on the test substance tested in the method of the present invention, so long as the test substance is thought to be used as a malodor inhibitor. The test substance may be a naturally occurring substance or a chemically or biologically synthesized artificial substance. The test substance may be a compound, a composition, or a mixture.

So long as the function of the olfactory receptor is not impaired, the olfactory receptor may be used in any form in the method of the present invention. For example, the olfactory receptor may be use in the following embodiments: tissues or cells which intrinsically express an olfactory receptor such as olfactory sensory neurons isolated from living bodies and cultured products thereof; olfactory cell membrane bearing the olfactory receptor; recombinant cells genetically modified so as to express the olfactory receptor and cultured products thereof; membrane of the recombinant cells; and artificial lipid bilayer membrane having the olfactory receptor. All of these embodiments are included within the scope of the olfactory receptor used in the present invention.

One preferred embodiment of the present invention employs cells which intrinsically express an olfactory receptor such as olfactory sensory neurons, recombinant cells genetically modified so as to express the olfactory receptor, or a cultured product of any of these. The recombinant cells may be produced through transformation by use of a vector to which a gene encoding the olfactory receptor has been incorporated. In this case, preferably in order to promote the expression of the olfactory receptor in the cellular membrane, RTP1S and receptor are transfected to cells.

An example of RTP1S that can be used in the production of the recombinant cell may be human RTP1S. Human RTP1S is registered in GenBank under Accession No. GI: 50234917. Human RTP1S is a protein consisting of the amino acid sequence set forth in SEQ ID NO: 12, which is encoded by a gene having the gene sequence set forth in SEQ ID NO: 11. Furthermore, instead of human RTP1S, a polypeptide consisting of an amino acid sequence having a sequence identity of 80% or more, preferably 85% or more, more preferably 90% or more, even more preferably 95% or more, and still more preferably 98% or more, with the amino acid sequence of human RTP1S (SEQ ID NO: 12), and which promotes, similarly to human RTP1S, the expression of olfactory receptors in the membrane, may also be used. For example, mouse RTP1S (see Sci Signal., 2009, 2(60): ra9 described above) is a protein which has a sequence identity of 89% with the amino acid sequence set forth in SEQ ID NO: 12, has a function of promoting the expression of olfactory receptors in the membrane, and can thus be used for the production of the recombinant cell described above.

In the present invention, the sequence identity (nucleotide sequence and amino acid sequence) is calculated through theLipman-Pearson method (Science, 227, 1435, (1985)). More specifically, the identity is calculated by a homology analysis program (Search homology) of the genetic information processing software Genetyx-Win (Ver. 5.1.1; Software Development) at a unit size to compare (ktup) of 2.

According to the method of the present invention, a test substance and a malodor-causing substance are added to an olfactory receptor, and then the response of the olfactory receptor to the malodor-causing substance is measured. The measurement may be performed through any method known in the art as a response measurement method of olfactory receptors; e.g., the calcium imaging method. When activated by an odorant molecule, an olfactory receptor activates adenylyl cyclase with the aid of $G\alpha s$ present in cells, to thereby elevate the intracellular cAMP level (Mombaerts P., Nat. Neurosci., 5, 263-278). Therefore, the response of an olfactory receptor can be measured by employing, as an index, the intracellular cAMP level determined after addition of the odorant. The method for determining the cAMP level employed in the present invention includes ELISA, reporter gene assay, and the like.

Next, the suppression effect of the test substance on the response of the olfactory receptor to a malodor-causing substance is evaluated on the basis of the measured response of the olfactory receptor, and the test substance that suppresses the response is identified. The evaluation of the suppression effect can be carried out by, for example, comparing the responses of the receptor to a malodor-causing substance measured when the test substance is added at different concentrations. As a more specific example, comparisons are made for the responses of the receptor to a malodor-causing substance between a test substance-added group with a higher concentration of the test substance and a test substance-added group with a lower concentration of the test substance; between a test substance-added group and a group without application; or between the response before the application of a test substance and the response after the application of a test substance. If the response of the olfactory receptor is suppressed by the addition of a test substance, or by the addition of a test substance at a higher concentration, the test substance can be identified as a substance which suppresses the response of the relevant olfactory receptor. For example, if the response of the receptor in a test substance-added group is suppressed to 80% or less, and preferably to 50% or less, as compared with a control group, the test substance can be selected as a malodor control agent.

The thus-identified test substance is a substance which suppresses the response of the olfactory receptor to the malodor employed in the above procedure, to thereby modulate the malodor recognition at the central nervous system through masking based on olfactory receptor antagonism, causing a subject to disable recognition of the malodor. Thus, the test substance identified in the above procedure is selected as a malodor inhibitor to the malodor employed in the above procedure.

According to another embodiment, the present invention provides a malodor inhibitor including an antagonist of an olfactory receptor to a malodor as an active ingredient. Examples of the malodor to be controlled include a hexanoic acid odor, a nonanoic acid odor, and an isovaleric acid odor. These odors are generally known as, for example, the odors of the body odor (or fatty acid odors) caused by sweat or sebum, or the like. Any one or more, and preferably all, of these odors are inhibited by the malodor inhibitor of the present invention.

The olfactory receptor related to the malodors may be any one olfactory receptor selected from the group consisting of OR51E1, OR2W1, OR10A6, OR51I2, and OR51L1. The antagonist as an active ingredient of the malodor inhibitor of the present invention may be an antagonist to any one of these olfactory receptors, or may be an antagonist to plural olfactory receptors. The olfactory receptors exhibit responses to the odor of nonanoic acid, hexanoic acid or isovaleric acid, as illustrated in FIGS. 1, 2, and 3. Therefore, when the responses of these receptors are suppressed, since a change occurs in the perception of the nonanoic acid odor, the hexanoic acid odor, or the isovaleric acid odor at the central nervous system, the malodor caused by nonanoic acid, hexanoic acid, or isovaleric acid can be inhibited through masking by means of the antagonism of olfactory receptors.

Examples of the antagonist include the substances indicated in the following Tables 1-1 and 1-2. As indicated in Table 3, these substances are antagonists of the relevant olfactory receptors, which control the response of the olfactory receptors. These substances have been traditionally known as fragrances, but it has not been known to date that these substances have olfactory receptor antagonist activity.

TABLE 1-1

| Name | Structure |
| --- | --- |
| 4-Isopropyl-1-methylcyclohexanecarbaldehyde | |
| Bourgeonal (3-(4-tert-butylphenyl)propanal) | |
| Cyclamen aldehyde (3-(4-isopropylphenyl)-2-methylpropanal) | |
| Florhydral (3-(3-isopropylphenyl)-butyraldehyde) | |
| Hydroxycitronellal (3,7-dimethyl-7-hydroxyoctanal) | |
| Lilial (p-tert-butyl-α-methylhydrocinnamaldehyde) | |
| Methoxycitronellal (7-methoxy-3,7-dimethyloctanal) | |
| Suzaral (3-(4-isobutylphenyl)-2-methyl-propionaldehyde) | |
| 4-Isopropyl-1-methylcyclohexylmethanol | |
| 4-(2-Methoxyphenyl)-2-methyl-2-butanol | |

TABLE 1-1-continued

| Name | Structure |
| --- | --- |
| Florosa (tetrahydro-4-methyl-2-(2-methylpropyl)-2H-pyran-4-ol) | 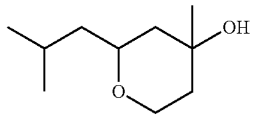 |

TABLE 1-2

| Name | Structure |
| --- | --- |
| Majantol (2,2-dimethyl-3-(3-methylphenyl)propanol) | 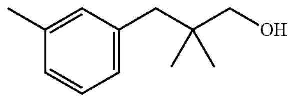 |
| 4-Isopropylcyclohexanecarbaldehyde | 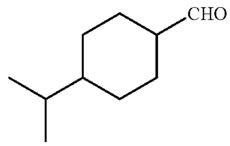 |
| Citronellal (3,7-dimethyl-6-octenal) | 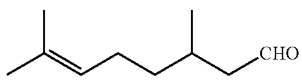 |
| Cyclemon A (1,2,3,4,5,6,7,8-octahydro-8,8-dimethyl-2-naphthalenecarboxyaldehyde) | 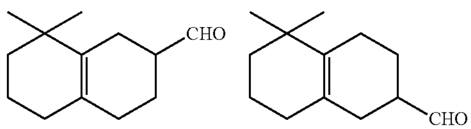 |
| Isocyclocitral (2,4,6-trimethyl-3-cyclohexene-1-carboxyaldehyde, 3,5,6-trimethyl-3-cyclohexene-1-carboxyaldehyde) | 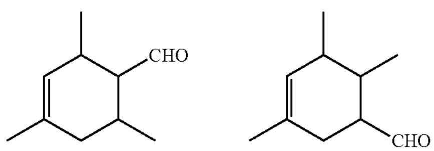 |
| Tripral (2,4-dimethyl-3-cyclohexane-1-carboxyaldehyde) | 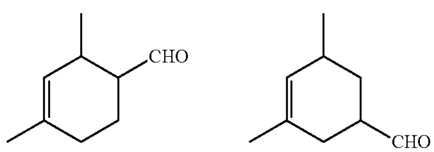 |
| Cuminaldehyde (4-isopropylbenzaldehyde) | 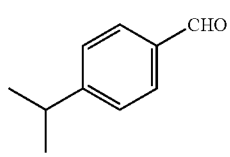 |
| Pollenal II (2-cyclohexylpropanol) | 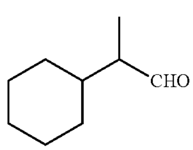 |

Among the antagonists described in Tables 1-1 and 1-2, preferred examples of the active ingredient of the malodor inhibitor of the present invention include florhydral, 4-isopropyl-1-methylcyclohexanecarbaldehyde, bourgeonal, hydroxycitronellal, 4-isopropylcyclohexanecarbaldehyde, 4-(2-methoxyphenyl)-2-methyl-2-butanol, florosa, cyclemon A, isocyclocitral, tripral, Pollenal II, and methoxycitronellal; and more preferred examples thereof include florhydral, bourgeonal, hydroxycitronellal, 4-isopropylcyclohexanecarbaldehyde, florosa, isocyclocitral, tripral, Pollenal II, and methoxycitronellal. Even more preferred examples thereof include florhydral, bourgeonal, methoxycitronellal, and isocyclocitral.

Among the antagonists described in Tables 1-1 and 1-2, bourgeonal (3-(4-tert-butylphenyl)propanal), florhydral (3-(3-isopropylphenyl)-butyraldehyde), lilial (p-tert-butyl-α- methylhydrocinnamaldehyde), and florosa (tetrahydro-4-methyl-2-(2-methylpropyl)-2H-pyran-4-ol) are available from Givaudan SA; Suzaral (3-(4-isobutylphenyl)-2-methylpropionaldehyde) is available from Takasago International Corp.; and majantol (2,2-dimethyl-3-(3-methylphenyl)propanol) is available from Symrise AG. Furthermore, cyclemon A (1,2,3,4,5,6,7,8-octahydro-8,8-dimethyl-2-naphthalenecarbox yaldehyde) and tripral (2,4-dimethyl-3-cyclohexane-1-carboxyaldehyde) are available from International Flavors & Fragrances, Inc.; and Pollenal II (2-cyclohexylpropanal) is available from Kao Corp. Cyclamen aldehyde (3-(4-isopropylphenyl)-2-methylpropanal), hydroxycitronellal (3,7-dimethyl-7-hydroxyoctanal), methoxycitronellal (7-methoxy-3,7-dimethyloctanal), citronellal (3,7-dimethyl-6-octenal), isocyclocitral (2,4,6-trimethyl-3-cyclohexene-1-carboxyaldehyde, 3,5,6-trimethyl-3-cyclohexene-1-carboxyaldehyde), and cuminaldehyde (4-isopropylbenzaldehyde) are available, as described in "Gosei Koryo Kagaku to Shohin Chishiki (Synthetic Fragrance and Flavor: Chemistry and Knowledge on Commercial Products), enlarged and revised edition, written by Indo, Motoichi, Chemical Daily Co., Ltd.," from International Flavors & Fragrances, Inc., Givaudan SA, Takasago International Corp., and the like. 4-Isopropyl-1-methylcyclohexanecarbaldehyde can be synthesized by, for example, a method described in JP-A-2009-149811. Furthermore, 4-isopropyl-1-methylcyclohexylmethanol can be synthesized by, for example, a method described in JP-A-2008-1667, and 4-(2-methoxyphenyl)-2-methyl-2-butanol can be synthesized by, for example, a method described in JP-A-09-111281.

For instance, 4-isopropylcyclohexanecarbaldehyde can be synthesized by a method described in JP-A-02-188549, by using 1554.57 g of 4-isopropylcyclohexylmethanol (Mayol; Firmenich SA) as a starting raw material, and the product thus obtainable is identified, for example, as follows:

$^{1}$H-NMR (CDCl$_{3}$, 400 MHz, δ ppm): 0.80 (3H, d, 6.8 Hz), 0.84 (3H, d, 6.8 Hz), 0.97-1.03, 1.19-1.30, 1.37-1.48, 1.51-1.61, 1.81-1.86, 1.95-1.99, 2.10-2.20 (10H, all m), 2.38-2.42 (1H, m), 9.56 (0.5H, s), 9.66 (0.5H, s)

$^{13}$C-NMR (CDCl$_{3}$, 100 MHz, δ ppm): 19.87, 19.92 (q), 24.79, 26.32, 26.57, 28.63 (t), 32.14, 32.84, 43.31, 43.60 (d), 47.18, 50.68 (d), 204.60, 205.51 (d)

The active ingredient of the malodor inhibitor of the present invention may be any one or more of the antagonists described above. That is, the malodor inhibitor of the present invention includes any of the aforementioned antagonists singly or in combination of two or more. Preferably, the malodor inhibitor of the present invention is essentially constituted of one or a combination of two or more of any of the antagonists described above.

According to another embodiment, the present invention provides a method for inhibiting malodor including causing a malodor and an antagonist of an olfactory receptor to the malodor to coexist. In this method, an antagonist of a receptor to a malodor is applied, in the presence of the malodor, to an individual in need of the inhibition of perception of the malodor, and preferably to an individual in need of the inhibition of perception of the malodor through masking by means of the antagonism of olfactory receptors, and the malodor and the antagonist are caused to coexist, or the antagonist is applied in advance to the individual, and then the malodor and the antagonist are caused to coexist. Thereby, the malodor receptor and the antagonist bind to each other, and thus the response of the receptor is suppressed. Accordingly, masking by means of the antagonism of olfactory receptors occurs, and the malodor is inhibited.

In the method of the present invention, the individual is not particularly limited as long as it is a mammal, but the individual is preferably a human being. The types of the malodor to be inhibited, the olfactory receptor, and the antagonist to be used are the same as in the case of the malodor inhibitor described above.

As will be described in the following Examples, the antagonists described in Tables 1-1 and 1-2 suppress the response of an olfactory receptor selected from the group consisting of OR51E1, OR2W1, OR10A6, OR51I2, and OR51L1 to the odor molecules. When the relevant antagonists are used, the odor originating from the odor molecules perceived by the olfactory receptor can be odor-specifically suppressed through masking by means of the antagonism of olfactory receptors.

The olfactory receptor antagonists described in Tables 1-1 and 1-2, or the malodor inhibitor selected according to the method for searching for a malodor inhibitor, can be used to inhibit the malodor through the olfactory masking based on the suppression of the response of an olfactory receptor to a malodor, and can also be used for the production of a compound or a composition intended to inhibit the malodor. In addition to the malodor inhibitor, the compound or composition for inhibiting malodor may appropriately include other components having a deodorizing effect or any arbitrary components used in deodorizers or disodorizers, for example, fragrances, powder components, liquid fat or oil, solid fat or oil, waxes, hydrocarbons, plant extracts, herbal medicine components, higher alcohols, lower alcohols, esters, long-chain fatty acids, surfactants (nonionic surfactants, anionic surfactants, cationic surfactants, amphoteric surfactants, and the like), sterols, polyhydric alcohols, moisture retainers, water-soluble polymer compounds, thickeners, film-forming agents, antibacterials, antiseptics, ultraviolet absorbers, fixing agents, cold sensation agents, temperature sensation agents, stimulants, metal ion sequestrants, sugars, amino acids, organic amines, synthetic resin emulsions, pH adjusting agents, oxidation inhibitors, oxidation inhibition aids, oils, powders, capsules, chelating agents, inorganic salts, organic salt dyes, antifungal agents, colorants, defoamants, extending agents, modulating agents, organic acids, polymers, polymer dispersants, enzymes, and enzyme stabilizers, according to the purpose.

As the other components having a deodorization effect that can be included in the compound or composition for malodor inhibition, any known deodorizer having a chemical or physical deodorization effect can be used, but examples that can be used include the deodorizing active ingredients extracted from various sites of plants such as leaves, leafstalks, fruits, stems, roots, and barks (for example, green tea extracts); organic acids such as lactic acid, gluconic acid, succinic acid, glutaric acid, adipic acid, malic acid, tartaric acid, maleic acid, fumaric acid, itaconic acid, citric acid, benzoic acid, and salicylic acid, various amino acids and salts thereof, glyoxal, oxidizing agents, flavonoids, catechins, polyphenols; porous materials such as activated carbon and zeolites; inclusion agents such as cyclodextrins; photocatalysts; and various masking agents.

EXAMPLES

Hereinafter, the present invention will be more specifically described by way of Examples.

Example 1

Identification of Olfactory Receptor Responding to Malodor

1) Cloning of Human Olfactory Receptor Genes

Cloning of human olfactory receptors was performed based on the sequence information registered in GenBank, through PCR with human genomic DNA female (G1521:

Promega) as a template. Each of the genes amplified through PCR was inserted into a pENTR vector (Invitrogen) according to an instruction manual. Then, the gene-inserted vector was digested with NotI and AscI, and the obtained fragments were inserted into NotI and AscI sites located downstream of the Flag-Rho tag sequence in the pME18S vector.

2) Production of pME18S-hRTP1S Vector

Cloning of human RTP1S was performed through PCR with a human RTP1 gene (MHS1010-9205862: Open Biosystems) as a template. EcoRI site was added to the forward primer employed in PCR, and XhoI site was added to the reverse primer. A hRTP1S gene (SEQ ID NO: 9) was amplified through PCR and inserted into EcoRI and XhoI site of the pME18S vector.

3) Production of Olfactory Receptor Expressing Cell

Each of the 350 types of human olfactory receptors was expressed in HEK293 cells. A reaction solution having a composition shown in Table 2 was prepared on a clean bench, and left to stand for 15 minutes. The solution was dispensed to each well of a 96-well plate (BD). Subsequently, HEK2.BR>X3 cells (100 µL, $3 \times 10^5$ cells/cm$^2$) were seeded in each well and cultured for 24 hours in an incubator at 37° C. and under 5% $CO_2$ conditions.

TABLE 2

| | |
|---|---|
| OPTI-MEM (GIBCO) | 50 µl |
| Human olfactory receptor gene | 0.075 µg |
| (Incorporated into a pME18S vector in which | |
| Flag-Rho tag is added to the N-terminus) | |
| pGL4.29 (fluc2P-CRE-hygro, Promega) | 0.03 µg |
| pGL4.75 (hRluc-CMV, Promega) | 0.03 µg |
| pME18S-hRTP1S | 0.03 µg |
| Lipofectamine 2000 (Invitrogen) | 0.4 µl |

4) Luciferase Assay

The olfactory receptor expressed in HEK293 cell was conjugated with cell-intrinsic Gαs to activate adenylate cyclase, and thereby the level of intracellular cAMP was increased. For the measurement of the response to odor in this study, the luciferase reporter gene assay was used, in which an increase in the amount of intracellular cAMP was monitored by using the emission value originating from firefly luciferase gene (fluc2P-CRE-hygro) as an indicator. Furthermore, a gene product obtained by fusing renilla luciferase gene in the downstream of CMV promoter (hRluc-CMV) was simultaneously introduced, and this was used as an internal standard for correcting an error in the transgenesis efficiency or the number of cells. The medium was removed from the culture prepared in the above-described section 3) by using a Pipetman, and 75 µl of a solution containing an odor substance (1 mM hexanoic acid or 300 µM nonanoic acid) prepared in CD293 medium (Invitrogen) was added thereto. The cells were cultured for 4 hours in a $CO_2$ incubator, and the luciferase gene was sufficiently expressed in the cells. For the measurement of luciferase activity, the measurement was carried out by using a Dual-Glow™ luciferase assay system (Promega) according to the operation manual of the product. A value calculated by dividing the emission value derived from a firefly luciferase induced by the stimulation with an odor substance, by the emission value in cells that were not stimulated with an odor substance, was designated as a fold increase, and used as an index of response intensity.

5) Results

Five olfactory receptors, namely, OR2W1, OR10A6, OR51E1, OR51I2, and OR51L1, exhibited response to hexanoic acid, and three olfactory receptors, namely, OR2W1, OR10A6, and OR51E1, exhibited response to nonanoic acid (FIG. 1).

Example 2

Response of Olfactory Receptors to Hexanoic Acid

The response of olfactory receptors OR2W1, OR10A6, OR51E1, OR51I2, and OR51L1, to hexanoic acid (0, 10, 30, 100, 300, and 1000 µM) was investigated by the same procedure as that used in Example 1. As a result, all of the olfactory receptors exhibited concentration-dependent response to hexanoic acid (FIG. 2).

Example 3

Response of Olfactory Receptors to Isovaleric Acid

The response of olfactory receptors OR2W1, OR10A6, OR51E1, OR51I2, and OR51L1, to isovaleric acid (0, 3, 10, 30, 100, 300, and 1000 µM) was investigated by the same procedure as that used in Example 1. Olfactory receptors OR51E1 and OR51I2 exhibited concentration-dependent response to isovaleric acid (FIG. 3).

Example 4

Identification of Malodor Control Agents

The inhibitory activity of fifty-two test substances on the olfactory receptor response was investigated, by using the olfactory receptors identified in Example 1 as the object of study.

OR2W1, OR10A6, OR51E1, OR51I2, and OR51L1 were respectively expressed in HEK293 cells by the same method as that used in Example 1, and a luciferase assay was carried out. In the luciferase assay, hexanoic acid was used as the odorous substance, and test substances were added together with hexanoic acid. The response of the olfactory receptors to hexanoic acid was measured, and a decrease in the receptor response to the addition of test substances was evaluated.

The inhibition ratios of the receptor response to test substances were calculated as follows. The emission value (Y) obtained from the cells in which the same receptors were introduced but no odor stimulation was conducted, was subtracted from the emission value derived from firefly luciferase (X) induced by odor stimulation with hexanoic acid alone. Similarly, the emission value (Y) obtained from the cells in which no odor stimulation was conducted, was subtracted from the emission value (Z) caused by stimulation with a mixture of hexanoic acid and a test substance. By the following calculation formula, the inhibitory activity of the test substance to receptor response was calculated based on the increment of the emission value (X−Y) caused by stimulation of hexanoic acid alone. Multiple independent experiments were performed in duplicate, and the average of each experiment was obtained.

$$\text{Inhibition ratio}(\%) = \{1 - (Z-Y)/(X-Y)\} \times 100$$

As a result, 7 test substances exhibited receptor response inhibitory activity on OR2W1, 3 test substances exhibited the same activity on OR10A6, 7 test substances exhibited the same activity on OR51E1, 10 test substances exhibited the same activity on OR51I2, and 6 test substances exhibited the same activity on OR51L1 (Table 3).

Figure 4:
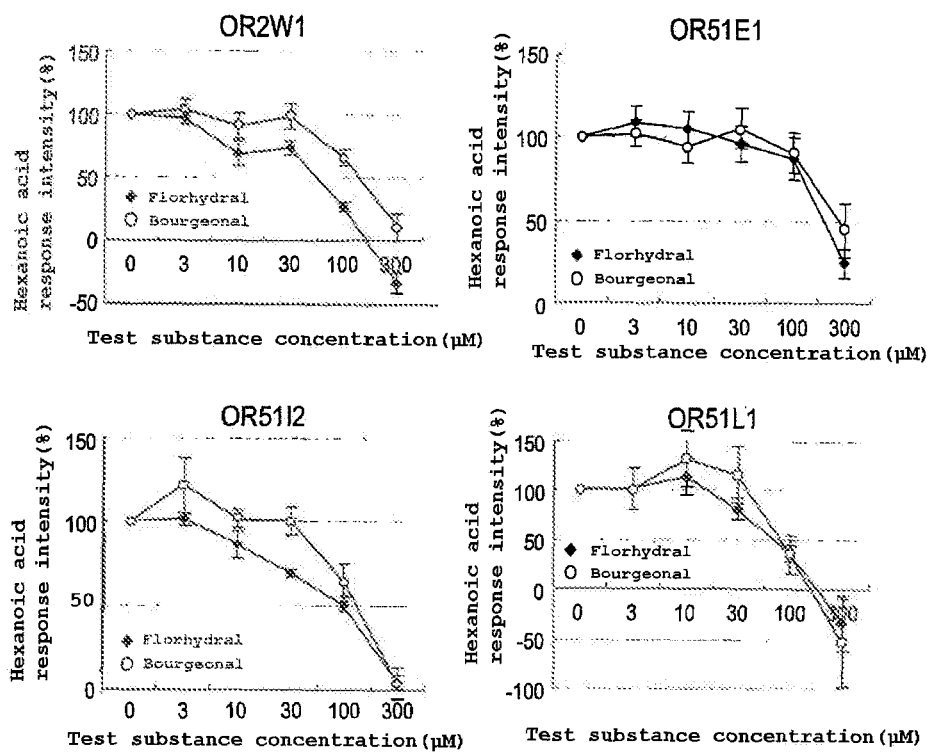
FIG. 4 is a set of diagrams illustrating the concentration-dependent inhibition of test substances in the response of receptors to hexanoic acid, in which an error bar=±SE.

Furthermore, with regard to some of the test substances that exhibited the inhibitory activity, concentration-dependent response inhibition of hexanoic acid response was investigated. The concentrations of the test substance used were 3, 10, 30, 100, and 300 μM. For the response of a receptor to 1 mM hexanoic acid at various test substance concentrations, the relative response intensity was investigated by designating the response intensity of the receptor at a test substance concentration of 0 μM, as 100%. As a result, it was found that, among the test substances which exhibited inhibitory activity, bourgeonal and florhydral inhibited the response of four olfactory receptors, namely, OR2W1, OR51E1, OR51I1, and OR51L1, to hexanoic acid all in a concentration-dependent manner (FIG. 4).

leric acid), and while the intensity of odor in the case of adding dropwise the malodor alone was rated as 5, the intensity of the malodor in the case of incorporating a test substance was evaluated on the basis of a system of 20 grades from 0 point to 10 points (0.5 points per grade).

Regarding the test substance, florhydral (Givaudan SA), bourgeonal (Givaudan SA), hydroxycitronellal (Givaudan SA, International Flavors & Fragrances, Inc., and the like), 4-isopropylcyclohexanecarbaldehyde (synthesized according to a method described in JP-A-2-188549), 4-(2-methoxyphenyl)-2-methyl-2-butanol (JP-A-9-111281), florosa (Givaudan SA), isocyclocitral (Givaudan SA, International Flavors & Fragrances, Inc., and the like), tripral (International Flavors & Fragrances, Inc.), and Pollenal II (Kao Corp.),

TABLE 3

| Odor molecule | 4-Isopropyl-1-methyl cyclohexanecarbaldehyde | Bourgeonal | Cyclamen aldehyde | Florhydral | Hydroxycitronellal |
|---|---|---|---|---|---|
| OR2W1  | — | 1 | — | 1 | — |
| OR51E1 | — | 1 | — | 1 | 2 |
| OR51L1 | — | 1 | — | 1 | 2 |
| OR51I2 | — | 1 | 2 | 1 | 2 |
| OR10A6 | 1 | — | — | — | — |

| Odor molecule | Lilial | Methoxycitronellal | Suzaral | 4-Isopropyl-1-methyl cyclohexylmethanol | 4-(2-Methoxyphenyl)-2-methyl-2-butanol |
|---|---|---|---|---|---|
| OR2W1  | 2 | — | — | — | 1 |
| OR51E1 | — | 1 | — | — | — |
| OR51L1 | — | 1 | — | — | — |
| OR51I2 | 2 | 1 | 2 | 2 | — |
| OR10A6 | — | — | — | — | — |

| Odor molecule | Florosa | Majantol | 4-Isopropylcyclo hexanecarbaldehyde | Citronellal | Cyclemon A |
|---|---|---|---|---|---|
| OR2W1  | — | 2 | — | — | 1 |
| OR51E1 | — | — | — | 2 | — |
| OR51L1 | — | — | — | — | — |
| OR51I2 | — | — | 2 | — | — |
| OR10A6 | 2 | — | — | — | — |

| Odor molecule | Isocyclocitral | Tripral | Cuminaldehyde | Pollenal II |
|---|---|---|---|---|
| OR2W1  | 1 | — | — | — |
| OR51E1 | 1 | — | — | 2 |
| OR51L1 | 1 | 2 | — | — |
| OR51I2 | — | — | 2 | — |
| OR10A6 | 1 | — | — | — |

1: Inhibition ratio: 50% or higher
2: Inhibition ratio: 20% to 50%

Example 5

Evaluation of Ability of Test Substances for Inhibiting Malodor

Test substances identified as having receptor response inhibitory activity in Example 4 were investigated for the abilities to suppress malodor by a sensory test.

Cotton balls were introduced into a glass bottle (Hakuyo Glass Co., Ltd. No. 11, capacity 110 ml), and hexanoic acid diluted 100 times with propylene glycol, nonanoic acid diluted 10 times with propylene glycol, or isovaleric acid diluted 1000 times with propylene glycol, as a malodor, and a test substance were added dropwise in an amount of 20 μl to the cotton balls. The glass bottle was left to stand overnight at room temperature, and the odor molecules were sufficiently volatilized in the glass bottle. A sensory evaluation test was carried out by a panel of three panelists (5 panelists for isova- which had been diluted 100 times with propylene glycol, were used for hexanoic acid; florhydral that had been diluted 10 times with propylene glycol was used for nonanoic acid; and florhydral that had been diluted 1000 times with propylene glycol was used for isovaleric acid. The same test was carried out on hexanoic acid by using, as a control substance for the test substance, fragrance floralol (diluted 100 times with propylene glycol), which was a substance having no response inhibiting effect on the olfactory receptors described above.

Figure 5:
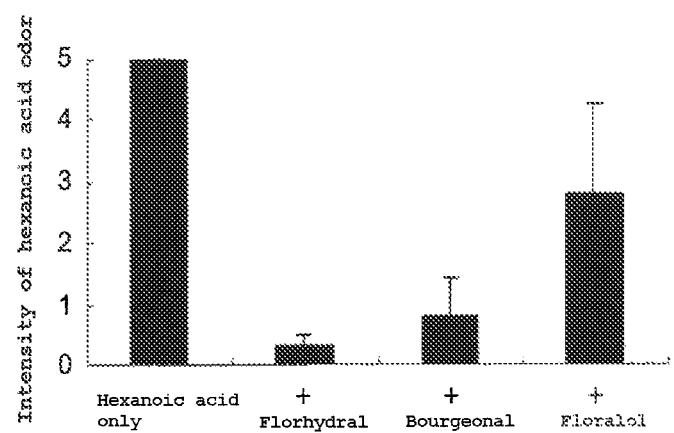
FIG. 5 is a diagram illustrating a sensory evaluation of the hexanoic acid odor control capacity of bourgeonal and florhydral, in which an error bar=±SE.
Figure 6:
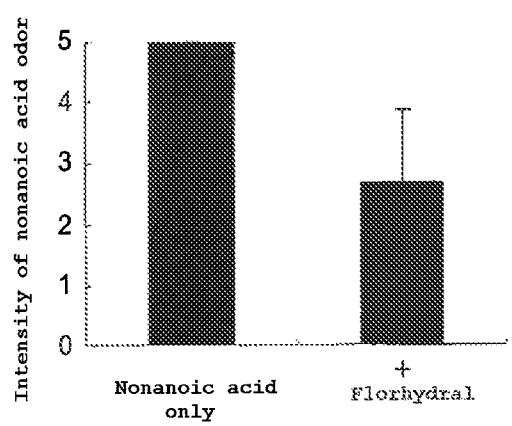
FIG. 6 is a diagram illustrating a sensory evaluation of the nonanoic acid odor control capacity of a test substance, in which an error bar=±SE.
Figure 7:
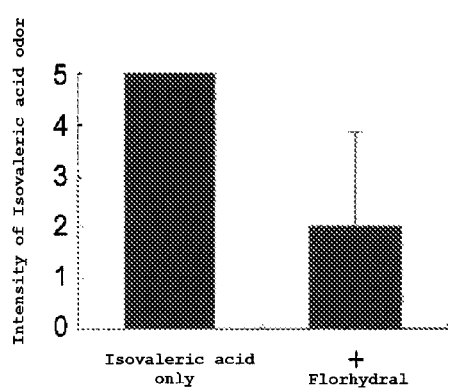
FIG. 7 is a diagram illustrating a sensory evaluation of the isovaleric acid odor control capacity of a test substance, in which an error bar=±SE.

Florhydral and bourgeonal, which inhibit the response of OR2W1, OR51E1, OR51I2, and OR51L1 to hexanoic acid, markedly inhibited the odor of hexanoic acid (FIG. 5). The inhibition of this hexanoic acid odor was significant as compared with the case of incorporating the control substance (floralol). Furthermore, the same investigation was conducted on nonanoic acid and isovaleric acid, and as a result, the odors were also inhibited by these test substances (FIGS. 6 and 7).

Meanwhile, the effect of inhibiting the hexanoic acid odor was also investigated on other substances that suppress the response of one kind or plural kinds of hexanoic acid receptors (hydroxycitronellal, 4-isopropylcyclohexanecarbaldehyde, 4-(2-methoxyphenyl)-2-methyl-2-butanol, florosa, isocyclocitral, tripral, and Pollenal II), and it was clarified that all of these test substances inhibit the hexanoic acid odor (Table 4).

TABLE 4

| Test substance | Intensity of odor |
| --- | --- |
| Hexanoic acid only | 5.00 |
| Bourgeonal | 3.13 |
| Florhydral | 1.25 |
| Hydroxycitronellal | 2.25 |
| 4-isopropylcyclohexanecarbaldehyde | 2.17 |
| 4-(2-methoxyphenyl)-2-methyl-2-butanol | 3.88 |
| Florosa | 3.38 |
| Isocyclocitral | 0.67 |

TABLE 4-continued

| Test substance | Intensity of odor |
| --- | --- |
| Tripral | 2.00 |
| Pollenal II | 2.08 |

In order to investigate the specificity of malodor inhibition by the test substances having receptor response inhibitory activity that had been identified in Example 4, the same sensory test was carried out by using cresol, which gives a malodor having a structure different from fatty acids and is an odor substance to which the olfactory receptors identified in Example 1 do not respond. In the experiment, cresol diluted 100 times with propylene glycol was used as the malodor, and florhydral diluted 100 times with propylene glycol was used as the test substance.

Figure 8:
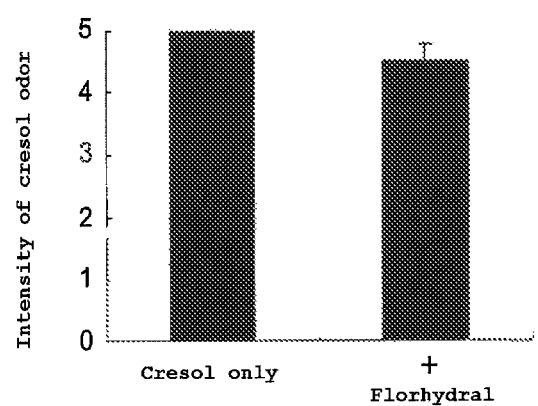
FIG. 8 is a diagram illustrating a sensory evaluation of the cresol odor control capacity of a test substance, in which an error bar=±SE.

As a result of the test, the odor of cresol was not inhibited by florhydral (FIG. 8). Therefore, it was found that the inhibiting effect is odor-specific.

The invention claimed is:

1. A method for searching for a malodor inhibitor, comprising:
   adding a test substance and a malodor-causing substance to any one olfactory receptor selected from the group consisting of OR51E1, OR2W1, OR10A6, and OR51I2;
   measuring the response of the olfactory receptor to the malodor-causing substance by measuring the response of the olfactory receptor in the presence and absence of the test substance;
   identifying a test substance that suppresses the response of the olfactory receptor on the basis of the response that was measured in the presence and absence of the test substance; and
   selecting the identified test substance as a malodor inhibitor, wherein
   when the receptor is OR51E1, the malodor-causing substance is hexanoic acid, nonanoic acid or isovaleric acid,
   when the receptor is OR2W1, the malodor-causing substance is hexanoic acid or nonanoic acid,
   when the receptor is OR10A6, the malodor-causing substance is hexanoic acid or nonanoic acid, and
   when the receptor is OR51I2, the malodor-causing substance is hexanoic acid or isovaleric acid.

2. The method according to claim 1, wherein the malodor is the odor of hexanoic acid.

3. The method according to claim 1, wherein the malodor is the odor of nonanoic acid.

4. The method according to claim 1, wherein the malodor is the odor of isovaleric acid.

5. The method according to claim 2, wherein the olfactory receptor is selected from the group consisting of OR51E1, OR10A6, and OR51I2.

6. The method according to claim 3, wherein the olfactory receptor is OR10A6.

7. The method according to claim 4, wherein the olfactory receptor is OR51I2.

8. The method according to claim 1, wherein the olfactory receptor is an olfactory receptor expressed on a cell which naturally expresses an olfactory receptor, or on a recombinant cell that has been genetically engineered so as to express an olfactory receptor.

9. The method according to claim 1, wherein when the response of the olfactory receptor to which the test substance has been added is suppressed to 80% or less relative to the response of the olfactory receptor to which the test substance has not been added, the test substance is selected as a malodor inhibitor.

10. The method according to claim 1, wherein the process of measuring the response of the receptor is carried out by a reporter gene assay.

11. The method of claim 1, further comprising carrying out a sensory evaluation test on the test substance that is identified as a test substance that suppresses the response of the olfactory receptor.

* * * * *

SEQUENCE LISTING

```
<160> NUMBER OF SEQ ID NOS: 12

<210> SEQ ID NO 1
<211> LENGTH: 945
<212> TYPE: DNA
<213> ORGANISM: Homo sapiens
<220> FEATURE:
<223> OTHER INFORMATION: OR10A6

<400> SEQUENCE: 1
atggaaagac aaaatcaaag ctgtgtggtt gaattcatcc tcttgggctt ttctaactat      60
cctgagctcc aggggcagct ctttgtggct ttcctggtta tttatctggt gaccctgata     120
ggaaatgcca ttattatagt catcgtctcc ctagaccaga gcctccacgt tcccatgtac     180
ctgtttctcc tgaacttatc tgtggtggac ctgagtttca gtgcagttat tatgcctgaa     240
atgctggtgg tcctctctac tgaaaaaact acaatttctt ttgggggctg ttttgcacag     300
atgtatttca tccttctttt tggtggggct gaatgttttc ttctgggagc aatggcttat     360
gaccgatttg ctgcaatttg ccatcctctc aactaccaaa tgattatgaa taaaggagtt     420
tttatgaaat taattatatt ttcatgggcc ttaggtttta tgttaggtac tgttcaaaca     480
tcatgggtat ctagttttcc cttttgtggc cttaatgaaa ttaaccatat atcttgtgaa     540 acccagcag tgttagaact tgcatgtgca gacacgtttt tgtttgaaat ctatgcattc     600
acaggcacct ttttgattat tttggttcct ttcttgttga tactcttgtc ttacattcga     660
gttctgtttg ccatcctgaa gatgccatca accactggga gacaaaaggc ctttccacc     720 tgtgccgctc acctcacatc tgtgaccccta ttctatggca cagccagtat gacttattta     780
caacccaaat ctggctactc accggaaacc aagaaagtga tgtcattgtc ttactcactt     840
ctgacaccac tgctgaatct gcttatctac agtttgcgaa atagtgagat gaagagggct     900
ttgatgaaat tatggcgaag gcgagtggtt ttacacacaa tctga                    945

<210> SEQ ID NO 2
<211> LENGTH: 314
<212> TYPE: PRT
<213> ORGANISM: Homo sapiens
<220> FEATURE:
<223> OTHER INFORMATION: OR10A6

<400> SEQUENCE: 2
```

```
Met Glu Arg Gln Asn Gln Ser Cys Val Val Glu Phe Ile Leu Leu Gly
1               5                   10                  15

Phe Ser Asn Tyr Pro Glu Leu Gln Gly Gln Leu Phe Val Ala Phe Leu
            20                  25                  30

Val Ile Tyr Leu Val Thr Leu Ile Gly Asn Ala Ile Ile Val Ile
        35                  40                  45

Val Ser Leu Asp Gln Ser Leu His Val Pro Met Tyr Leu Phe Leu Leu
50                  55                  60

Asn Leu Ser Val Val Asp Leu Ser Phe Ser Ala Val Ile Met Pro Glu
65                  70                  75                  80

Met Leu Val Val Leu Ser Thr Glu Lys Thr Thr Ile Ser Phe Gly Gly
                85                  90                  95

Cys Phe Ala Gln Met Tyr Phe Ile Leu Leu Phe Gly Gly Ala Glu Cys
                100                 105                 110

Phe Leu Leu Gly Ala Met Ala Tyr Asp Arg Phe Ala Ala Ile Cys His
            115                 120                 125

Pro Leu Asn Tyr Gln Met Ile Met Asn Lys Gly Val Phe Met Lys Leu
        130                 135                 140

Ile Ile Phe Ser Trp Ala Leu Gly Phe Met Leu Gly Thr Val Gln Thr
145                 150                 155                 160

Ser Trp Val Ser Ser Phe Pro Phe Cys Gly Leu Asn Glu Ile Asn His
                165                 170                 175

Ile Ser Cys Glu Thr Pro Ala Val Leu Glu Leu Ala Cys Ala Asp Thr
                180                 185                 190

Phe Leu Phe Glu Ile Tyr Ala Phe Thr Gly Thr Phe Leu Ile Ile Leu
            195                 200                 205

Val Pro Phe Leu Leu Ile Leu Leu Ser Tyr Ile Arg Val Leu Phe Ala
        210                 215                 220

Ile Leu Lys Met Pro Ser Thr Thr Gly Arg Gln Lys Ala Phe Ser Thr
225                 230                 235                 240

Cys Ala Ala His Leu Thr Ser Val Thr Leu Phe Tyr Gly Thr Ala Ser
                245                 250                 255

Met Thr Tyr Leu Gln Pro Lys Ser Gly Tyr Ser Pro Glu Thr Lys Lys
            260                 265                 270

Val Met Ser Leu Ser Tyr Ser Leu Leu Thr Pro Leu Leu Asn Leu Leu
        275                 280                 285

Ile Tyr Ser Leu Arg Asn Ser Glu Met Lys Arg Ala Leu Met Lys Leu
        290                 295                 300

Trp Arg Arg Arg Val Val Leu His Thr Ile
305                 310
```

<210> SEQ ID NO 3
<211> LENGTH: 963
<212> TYPE: DNA
<213> ORGANISM: Homo sapiens
<220> FEATURE:
<223> OTHER INFORMATION: OR2W1

<400> SEQUENCE: 3

```
atggaccaaa gcaattatag ttctttacat ggttttattc tgcttggctt ctctaaccat      60
ccaaaaatgg agatgatcct gtcaggagtt gtcgccatct tctacttaat tacattggtg     120
ggtaacacag ccatcattct tgcatctctc ctggattccc agcttcatac accaatgtac     180
tttttcctca gaaatttatc tttcctagat ctatgtttca aaccagcat catccctcag      240
```

| | |
|---|---|
| atgctggtca acttgtgggg acctgataag accatcagct atgtgggttg tatcatccaa | 300 |
| ctctatgttt acatgtggtt gggctcagtt gagtgccttc tcctggctgt tatgtcctat | 360 |
| gatcgtttta cagctatatg taagcccttg cattattttg tagtcatgaa cccacatcta | 420 |
| tgtctaaaga tgattatcat gatctggagt attagtttgg ccaattctgt agtattatgt | 480 |
| acactcactc tgaatttgcc cacatgtgga acaacattc tggatcattt cttgtgtgag | 540 |
| ttgccagctc tggtcaagat agcttgtgta gacaccacaa cagttgaaat gtctgttttc | 600 |
| gctttaggca ttataattgt cctcacacct ctcatcctta ttcttatatc ctatggctac | 660 |
| attgccaaag ctgtgctgag aacgaagtca aaagcaagcc agcgaaaagc aatgaatacc | 720 |
| tgtggatctc atcttactgt agtgtctatg ttctatggaa ctattatcta catgtacctg | 780 |
| caaccaggta acagggcttc caaagaccag ggcaagttcc tcaccctctt ttacaccgtc | 840 |
| atcactccaa gtctcaaccc gctcatttac accttaagaa ataaggacat gaaggatgcc | 900 |
| ctgaagaaac tgatgagatt tcaccacaaa tctacaaaaa taaagaggaa ttgcaagtca | 960 |
| tag | 963 |

<210> SEQ ID NO 4
<211> LENGTH: 320
<212> TYPE: PRT
<213> ORGANISM: Homo sapiens
<220> FEATURE:
<223> OTHER INFORMATION: OR2W1

<400> SEQUENCE: 4

Met Asp Gln Ser Asn Tyr Ser Ser Leu His Gly Phe Ile Leu Leu Gly
1               5                   10                  15

Phe Ser Asn His Pro Lys Met Glu Met Ile Leu Ser Gly Val Val Ala
            20                  25                  30

Ile Phe Tyr Leu Ile Thr Leu Val Gly Asn Thr Ala Ile Ile Leu Ala
        35                  40                  45

Ser Leu Leu Asp Ser Gln Leu His Thr Pro Met Tyr Phe Phe Leu Arg
    50                  55                  60

Asn Leu Ser Phe Leu Asp Leu Cys Phe Thr Thr Ser Ile Ile Pro Gln
65                  70                  75                  80

Met Leu Val Asn Leu Trp Gly Pro Asp Lys Thr Ile Ser Tyr Val Gly
                85                  90                  95

Cys Ile Ile Gln Leu Tyr Val Tyr Met Trp Leu Gly Ser Val Glu Cys
            100                 105                 110

Leu Leu Leu Ala Val Met Ser Tyr Asp Arg Phe Thr Ala Ile Cys Lys
        115                 120                 125

Pro Leu His Tyr Phe Val Val Met Asn Pro His Leu Cys Leu Lys Met
    130                 135                 140

Ile Ile Met Ile Trp Ser Ile Ser Leu Ala Asn Ser Val Val Leu Cys
145                 150                 155                 160

Thr Leu Thr Leu Asn Leu Pro Thr Cys Gly Asn Asn Ile Leu Asp His
                165                 170                 175

Phe Leu Cys Glu Leu Pro Ala Leu Val Lys Ile Ala Cys Val Asp Thr
            180                 185                 190

Thr Thr Val Glu Met Ser Val Phe Ala Leu Gly Ile Ile Ile Val Leu
        195                 200                 205

Thr Pro Leu Ile Leu Ile Leu Ile Ser Tyr Gly Tyr Ile Ala Lys Ala
    210                 215                 220

Val Leu Arg Thr Lys Ser Lys Ala Ser Gln Arg Lys Ala Met Asn Thr

```
                225                 230                 235                 240
Cys Gly Ser His Leu Thr Val Val Ser Met Phe Tyr Gly Thr Ile Ile
                245                 250                 255

Tyr Met Tyr Leu Gln Pro Gly Asn Arg Ala Ser Lys Asp Gln Gly Lys
                260                 265                 270

Phe Leu Thr Leu Phe Tyr Thr Val Ile Thr Pro Ser Leu Asn Pro Leu
                275                 280                 285

Ile Tyr Thr Leu Arg Asn Lys Asp Met Lys Asp Ala Leu Lys Lys Leu
                290                 295                 300

Met Arg Phe His His Lys Ser Thr Lys Ile Lys Arg Asn Cys Lys Ser
305                 310                 315                 320

<210> SEQ ID NO 5
<211> LENGTH: 954
<212> TYPE: DNA
<213> ORGANISM: Homo sapiens
<220> FEATURE:
<223> OTHER INFORMATION: OR51E1

<400> SEQUENCE: 5
atgatggtgg atcccaatgg caatgaatcc agtgctacat acttcatcct aataggcctc      60
cctggtttag aagaggctca gttctggttg ccttcccat tgtgctccct ctaccttatt      120
gctgtgctag gtaacttgac aatcatctac attgtgcgga ctgagcacag cctgcatgag      180
cccatgtata tatttctttg catgctttca ggcattgaca tcctcatctc cacctcatcc      240
atgcccaaaa tgctggccat cttctggttc aattccacta ccatccagtt tgatgcttgt      300
ctgctacaga tgttttgccat ccactcctta tctggcatgg aatccacagt gctgctggcc      360
atggcttttg accgctatgt ggccatctgt cacccactgc gccatgccac agtacttacg      420
ttgcctcgtg tcaccaaaaat tggtgtggct gctgtgtgc gggggggctgc actgatggca      480
ccccttcctg tcttcatcaa gcagctgccc ttctgccgct ccaatatcct ttcccattcc      540
tactgcctac accaagatgt catgaagctg gcctgtgatg atatccgggt caatgtcgtc      600
tatggcctta tcgtcatcat ctccgccatt ggcctggact cacttctcat ctccttctca      660
tatctgctta ttcttaagac tgtgttgggc ttgacacgtg aagcccaggc caaggcattt      720
ggcacttgcg tctctcatgt gtgtgctgtg ttcatattct atgtaccttt cattggattg      780
tccatggtgc atcgctttag caagcggcgt gactctccgc tgcccgtcat cttggccaat      840
atctatctgc tggttcctcc tgtgctcaac ccaattgtct atggagtgaa gacaaaggag      900
attcgacagc gcatccttcg acttttccat gtggccacac acgcttcaga gccc            954

<210> SEQ ID NO 6
<211> LENGTH: 318
<212> TYPE: PRT
<213> ORGANISM: Homo sapiens
<220> FEATURE:
<223> OTHER INFORMATION: OR51E1

<400> SEQUENCE: 6

Met Met Val Asp Pro Asn Gly Asn Glu Ser Ser Ala Thr Tyr Phe Ile
1               5                   10                  15

Leu Ile Gly Leu Pro Gly Leu Glu Glu Ala Gln Phe Trp Leu Ala Phe
                20                  25                  30

Pro Leu Cys Ser Leu Tyr Leu Ile Ala Val Leu Gly Asn Leu Thr Ile
                35                  40                  45

Ile Tyr Ile Val Arg Thr Glu His Ser Leu His Glu Pro Met Tyr Ile
```

```
            50                  55                  60
Phe Leu Cys Met Leu Ser Gly Ile Asp Ile Leu Ile Ser Thr Ser Ser
 65                  70                  75                  80

Met Pro Lys Met Leu Ala Ile Phe Trp Phe Asn Ser Thr Thr Ile Gln
                 85                  90                  95

Phe Asp Ala Cys Leu Leu Gln Met Phe Ala Ile His Ser Leu Ser Gly
            100                 105                 110

Met Glu Ser Thr Val Leu Leu Ala Met Ala Phe Asp Arg Tyr Val Ala
        115                 120                 125

Ile Cys His Pro Leu Arg His Ala Thr Val Leu Thr Leu Pro Arg Val
130                 135                 140

Thr Lys Ile Gly Val Ala Ala Val Val Arg Gly Ala Ala Leu Met Ala
145                 150                 155                 160

Pro Leu Pro Val Phe Ile Lys Gln Leu Pro Phe Cys Arg Ser Asn Ile
                165                 170                 175

Leu Ser His Ser Tyr Cys Leu His Gln Asp Val Met Lys Leu Ala Cys
            180                 185                 190

Asp Asp Ile Arg Val Asn Val Val Tyr Gly Leu Ile Val Ile Ile Ser
        195                 200                 205

Ala Ile Gly Leu Asp Ser Leu Leu Ile Ser Phe Ser Tyr Leu Leu Ile
210                 215                 220

Leu Lys Thr Val Leu Gly Leu Thr Arg Glu Ala Gln Ala Lys Ala Phe
225                 230                 235                 240

Gly Thr Cys Val Ser His Val Cys Ala Val Phe Ile Phe Tyr Val Pro
                245                 250                 255

Phe Ile Gly Leu Ser Met Val His Arg Phe Ser Lys Arg Arg Asp Ser
            260                 265                 270

Pro Leu Pro Val Ile Leu Ala Asn Ile Tyr Leu Leu Val Pro Pro Val
        275                 280                 285

Leu Asn Pro Ile Val Tyr Gly Val Lys Thr Lys Glu Ile Arg Gln Arg
        290                 295                 300

Ile Leu Arg Leu Phe His Val Ala Thr His Ala Ser Glu Pro
305                 310                 315

<210> SEQ ID NO 7
<211> LENGTH: 936
<212> TYPE: DNA
<213> ORGANISM: Homo sapiens
<220> FEATURE:
<223> OTHER INFORMATION: OR51I2

<400> SEQUENCE: 7 atgggggttgt tcaatgtcac tcaccctgca ttcttcctcc tgactggtat ccctggtctg      60
gagagctctc actcctggct gtcagggccc ctctgcgtga tgtatgctgt ggcccttggg     120
ggaaatacag tgatcctgca ggctgtgcga gtggagccca gctccatga gcccatgtac      180 tacttcctgt ccatgttgtc cttcagtgat gtggccatat ccatggccac actgccact      240 gtactccgaa ccttctgcct caatgcccgc aacatcactt tgatgcctg tctaattcag     300 atgtttctta ttcacttctt ctccatgatg aatcaggta ttctgctggc catgagtttt    360
gaccgctatg tggccatttg tgacccctg cgctatgcaa ctgtgctcac cactgaagtc      420
attgctgcaa tgggtttagg tgcagctgct cgaagcttca tcacccttt ccctcttccc     480 tttcttatta gaggctgcc tatctgcaga tccaatgttc tttctcactc ctactgcctg     540
cacccagaca tgatgaggct tgcctgtgct gatatcagta tcaacagcat ctatggactc      600
```

```
tttgttcttg tatccacctt tggcatggac ctgttttta tcttcctctc ctatgtgctc      660
attctgcgtt ctgtcatggc cactgcttcc cgtgaggaac gcctcaaagc tctcaacaca      720
tgtgtgtcac atatcctggc tgtacttgca ttttatgtgc caatgattgg ggtctccaca      780
gtgcaccgct ttgggaagca tgtcccatgc tacatacatg tcctcatgtc aaatgtgtac      840
ctatttgtgc ctcctgtgct caaccctctc atttatagcg ccaagacaaa ggaaatccgc      900
cgagccattt tccgcatgtt tcaccacatc aaaata                                936
```

<210> SEQ ID NO 8
<211> LENGTH: 312
<212> TYPE: PRT
<213> ORGANISM: Homo sapiens
<220> FEATURE:
<223> OTHER INFORMATION: OR51I2

<400> SEQUENCE: 8

```
Met Gly Leu Phe Asn Val Thr His Pro Ala Phe Phe Leu Leu Thr Gly
 1               5                  10                  15

Ile Pro Gly Leu Glu Ser Ser His Ser Trp Leu Ser Gly Pro Leu Cys
             20                  25                  30

Val Met Tyr Ala Val Ala Leu Gly Gly Asn Thr Val Ile Leu Gln Ala
         35                  40                  45

Val Arg Val Glu Pro Ser Leu His Glu Pro Met Tyr Tyr Phe Leu Ser
     50                  55                  60

Met Leu Ser Phe Ser Asp Val Ala Ile Ser Met Ala Thr Leu Pro Thr
 65                  70                  75                  80

Val Leu Arg Thr Phe Cys Leu Asn Ala Arg Asn Ile Thr Phe Asp Ala
                 85                  90                  95

Cys Leu Ile Gln Met Phe Leu Ile His Phe Phe Ser Met Met Glu Ser
            100                 105                 110

Gly Ile Leu Leu Ala Met Ser Phe Asp Arg Tyr Val Ala Ile Cys Asp
        115                 120                 125

Pro Leu Arg Tyr Ala Thr Val Leu Thr Thr Glu Val Ile Ala Ala Met
    130                 135                 140

Gly Leu Gly Ala Ala Ala Arg Ser Phe Ile Thr Leu Phe Pro Leu Pro
145                 150                 155                 160

Phe Leu Ile Lys Arg Leu Pro Ile Cys Arg Ser Asn Val Leu Ser His
                165                 170                 175

Ser Tyr Cys Leu His Pro Asp Met Met Arg Leu Ala Cys Ala Asp Ile
            180                 185                 190

Ser Ile Asn Ser Ile Tyr Gly Leu Phe Val Leu Val Ser Thr Phe Gly
        195                 200                 205

Met Asp Leu Phe Phe Ile Phe Leu Ser Tyr Val Leu Ile Leu Arg Ser
    210                 215                 220

Val Met Ala Thr Ala Ser Arg Glu Glu Arg Leu Lys Ala Leu Asn Thr
225                 230                 235                 240

Cys Val Ser His Ile Leu Ala Val Leu Ala Phe Tyr Val Pro Met Ile
                245                 250                 255

Gly Val Ser Thr Val His Arg Phe Gly Lys His Val Pro Cys Tyr Ile
            260                 265                 270

His Val Leu Met Ser Asn Val Tyr Leu Phe Val Pro Pro Val Leu Asn
        275                 280                 285

Pro Leu Ile Tyr Ser Ala Lys Thr Lys Glu Ile Arg Arg Ala Ile Phe
    290                 295                 300
```

Arg Met Phe His His Ile Lys Ile
305                 310

<210> SEQ ID NO 9
<211> LENGTH: 945
<212> TYPE: DNA
<213> ORGANISM: Homo sapiens
<220> FEATURE:
<223> OTHER INFORMATION: OR51L1

<400> SEQUENCE: 9

| | | | | | |
|---|---|---|---|---|---|
| atgggagact | ggaataacag | tgatgctgtg | gagcccatat | ttatcctgag | gggttttcct | 60 |
| ggactggagt | atgttcattc | ttggctctcc | atcctcttct | gtcttgcata | tttggtagca | 120 |
| tttatgggta | atgttaccat | cctgtctgtc | atttggatag | aatcctctct | ccatcagccc | 180 |
| atgtattact | ttatttccat | cttagcagtg | aatgacctgg | ggatgtccct | gtctacactt | 240 |
| cccaccatgc | ttgctgtgtt | atggttggat | gctccagaga | tccaggcaag | tgcttgctat | 300 |
| gctcagctgt | tcttcatcca | cacattcaca | ttcctggagt | cctcagtgtt | gctggccatg | 360 |
| gcctttgacc | gttttgttgc | tatctgccat | ccactgcact | accccaccat | cctcaccaac | 420 |
| agtgtaattg | gcaaaattgg | tttggcctgt | ttgctacgaa | gcttgggagt | tgtacttccc | 480 |
| acacctttgc | tactgagaca | ctatcactac | tgccatggca | atgccctctc | tcacgccttc | 540 |
| tgtttgcacc | aggatgttct | aagattatcc | tgtacagatg | ccaggaccaa | cagtatttat | 600 |
| gggctttgtg | tagtcattgc | cacactaggt | gtggattcaa | tcttcatact | tctttcttat | 660 |
| gttctgattc | ttaatactgt | gctggatatt | gcatctcgtg | aagagcagct | aaaggcactc | 720 |
| aacacatgtg | tatcccatat | ctgtgtggtg | cttatcttct | ttgtgccagt | tattggggtg | 780 |
| tcaatggtcc | atcgctttgg | gaagcatctg | tctcccatag | tccacatcct | catggcagac | 840 |
| atctaccttc | ttcttccccc | agtccttaac | cctattgtct | atagtgtcag | aacaaagcag | 900 |
| attcgtctag | gaattctcca | caagtttgtc | ctaaggagga | ggttt | 945 |

<210> SEQ ID NO 10
<211> LENGTH: 315
<212> TYPE: PRT
<213> ORGANISM: Homo sapiens
<220> FEATURE:
<223> OTHER INFORMATION: OR51L1

<400> SEQUENCE: 10

Met Gly Asp Trp Asn Asn Ser Asp Ala Val Glu Pro Ile Phe Ile Leu
1               5                   10                  15

Arg Gly Phe Pro Gly Leu Glu Tyr Val His Ser Trp Leu Ser Ile Leu
            20                  25                  30

Phe Cys Leu Ala Tyr Leu Val Ala Phe Met Gly Asn Val Thr Ile Leu
        35                  40                  45

Ser Val Ile Trp Ile Glu Ser Ser Leu His Gln Pro Met Tyr Tyr Phe
    50                  55                  60

Ile Ser Ile Leu Ala Val Asn Asp Leu Gly Met Ser Leu Ser Thr Leu
65                  70                  75                  80

Pro Thr Met Leu Ala Val Leu Trp Leu Asp Ala Pro Glu Ile Gln Ala
                85                  90                  95

Ser Ala Cys Tyr Ala Gln Leu Phe Phe Ile His Thr Phe Thr Phe Leu
            100                 105                 110

Glu Ser Ser Val Leu Leu Ala Met Ala Phe Asp Arg Phe Val Ala Ile
        115                 120                 125

```
Cys His Pro Leu His Tyr Pro Thr Ile Leu Thr Asn Ser Val Ile Gly
        130                 135                 140

Lys Ile Gly Leu Ala Cys Leu Leu Arg Ser Leu Gly Val Val Leu Pro
145                 150                 155                 160

Thr Pro Leu Leu Leu Arg His Tyr His Tyr Cys His Gly Asn Ala Leu
                165                 170                 175

Ser His Ala Phe Cys Leu His Gln Asp Val Leu Arg Leu Ser Cys Thr
            180                 185                 190

Asp Ala Arg Thr Asn Ser Ile Tyr Gly Leu Cys Val Val Ile Ala Thr
        195                 200                 205

Leu Gly Val Asp Ser Ile Phe Ile Leu Leu Ser Tyr Val Leu Ile Leu
    210                 215                 220

Asn Thr Val Leu Asp Ile Ala Ser Arg Glu Glu Gln Leu Lys Ala Leu
225                 230                 235                 240

Asn Thr Cys Val Ser His Ile Cys Val Val Leu Ile Phe Phe Val Pro
                245                 250                 255

Val Ile Gly Val Ser Met Val His Arg Phe Gly Lys His Leu Ser Pro
            260                 265                 270

Ile Val His Ile Leu Met Ala Asp Ile Tyr Leu Leu Pro Pro Val
        275                 280                 285

Leu Asn Pro Ile Val Tyr Ser Val Arg Thr Lys Gln Ile Arg Leu Gly
    290                 295                 300

Ile Leu His Lys Phe Val Leu Arg Arg Arg Phe
305                 310                 315

<210> SEQ ID NO 11
<211> LENGTH: 684
<212> TYPE: DNA
<213> ORGANISM: Homo sapiens
<220> FEATURE:
<223> OTHER INFORMATION: RTP1S

<400> SEQUENCE: 11
atgtgtaaaa gcgtgaccac agatgagtgg aagaaagtct tctatgagaa gatggaggag    60
gcaaagccgg ctgacagctg ggacctcatc atagacccca acctcaagca caatgtgctg   120
agccctggtt ggaagcagta cctggaattg catgcttcag gcaggttcca ctgctcctgg   180
tgctggcaca cctggcagtc gccctacgtg gtcatcctct ccacatgtt cctgaccgc     240 gcccagcggg cgggctcggt gcgcatgcgc gtcttcaagc agctgtgcta tgagtgcggc   300
acggcgcggc tggacgagtc cagcatgctg gaggagaaca tcgagggcct ggtggacaac   360
ctcatcacca gcctgcgcga gcagtgctac ggcgagcgtg gcggccagta ccgcatccac   420
gtggccagcc gccaggacaa ccggcggcac cgcggagagt ctgcgaggc ctgccaggag    480 ggcatcgtgc actggaagcc cagcgagaag ctgctggagg aggaggcgac cacctacacc   540
ttctcccggg cgcccagccc caccaagtcg caggaccaga cgggctcagg ctggaacttc   600
tgctctatcc cctggtgctt gttttgggcc acggtcctgc tgctgatcat ctacctgcag   660
ttctctttcc gtagctccgt ataa                                          684

<210> SEQ ID NO 12
<211> LENGTH: 227
<212> TYPE: PRT
<213> ORGANISM: Homo sapiens
<220> FEATURE:
<223> OTHER INFORMATION: RTP1S
```

```
<400> SEQUENCE: 12

Met Cys Lys Ser Val Thr Thr Asp Glu Trp Lys Lys Val Phe Tyr Glu
1               5                   10                  15

Lys Met Glu Glu Ala Lys Pro Ala Asp Ser Trp Asp Leu Ile Ile Asp
            20                  25                  30

Pro Asn Leu Lys His Asn Val Leu Ser Pro Gly Trp Lys Gln Tyr Leu
            35                  40                  45

Glu Leu His Ala Ser Gly Arg Phe His Cys Ser Trp Cys Trp His Thr
        50                  55                  60

Trp Gln Ser Pro Tyr Val Val Ile Leu Phe His Met Phe Leu Asp Arg
65                  70                  75                  80

Ala Gln Arg Ala Gly Ser Val Arg Met Arg Val Phe Lys Gln Leu Cys
                85                  90                  95

Tyr Glu Cys Gly Thr Ala Arg Leu Asp Glu Ser Ser Met Leu Glu Glu
                100                 105                 110

Asn Ile Glu Gly Leu Val Asp Asn Leu Ile Thr Ser Leu Arg Glu Gln
                115                 120                 125

Cys Tyr Gly Glu Arg Gly Gly Gln Tyr Arg Ile His Val Ala Ser Arg
130                 135                 140

Gln Asp Asn Arg Arg His Arg Gly Glu Phe Cys Glu Ala Cys Gln Glu
145                 150                 155                 160

Gly Ile Val His Trp Lys Pro Ser Glu Lys Leu Leu Glu Glu Glu Ala
                165                 170                 175

Thr Thr Tyr Thr Phe Ser Arg Ala Pro Ser Pro Thr Lys Ser Gln Asp
                180                 185                 190

Gln Thr Gly Ser Gly Trp Asn Phe Cys Ser Ile Pro Trp Cys Leu Phe
            195                 200                 205

Trp Ala Thr Val Leu Leu Leu Ile Ile Tyr Leu Gln Phe Ser Phe Arg
        210                 215                 220

Ser Ser Val
225
```